United States Patent
Richard

(10) Patent No.: US 7,354,571 B2
(45) Date of Patent: Apr. 8, 2008

(54) PHOTOPROTECTIVE COMPOSITIONS COMPRISING METHYLTRIALKYLSILANES CONTAINING A CINNAMATE, CINNAMAMIDE, BENZALMALONAMIDE OR BENZALMALONATE FUNCTION

(75) Inventor: Herve Richard, Villepinte (FR)

(73) Assignee: L'Oreal, Paris (FR)

( * ) Notice: Subject to any disclaimer, the term of this patent is extended or adjusted under 35 U.S.C. 154(b) by 405 days.

(21) Appl. No.: 11/189,975

(22) Filed: Jul. 27, 2005

(65) Prior Publication Data

US 2006/0018848 A1    Jan. 26, 2006

Related U.S. Application Data

(63) Continuation of application No. PCT/EP03/15038, filed on Dec. 19, 2003.

(60) Provisional application No. 60/450,708, filed on Mar. 3, 2003.

(30) Foreign Application Priority Data

Jan. 28, 2003    (FR) .................................. 03 00909

(51) Int. Cl.
- *A61Q 17/04* (2006.01)
- *A61Q 17/00* (2006.01)
- *A61Q 19/04* (2006.01)
- *A61Q 19/00* (2006.01)
- *A61K 8/02* (2006.01)

(52) U.S. Cl. .......................... 424/59; 424/60; 424/400; 424/401

(58) Field of Classification Search ................ 424/59, 424/60, 400, 401; 514/63; 524/261; 556/419, 556/437

See application file for complete search history.

(56) References Cited

U.S. PATENT DOCUMENTS 6,488,915 B1 * 12/2002 Heidenfelder et al. ........ 424/59

FOREIGN PATENT DOCUMENTS

| EP | 0 868 905 A2 | 10/1998 |
| EP | 1 269 979 A1 | 1/2003 |
| JP | 07 330779 A | 4/1996 |

OTHER PUBLICATIONS

Palomo et al., "Fluoride ion mediated Peterson alkenylation of N-'C,C-bis(trimethylsilyl)methyl amido derivatives with carbonyl compounds: a short general route to enamides and 1,2-dihydroisoquinolines", Database accession No. 117:131040, XP 002248430, abstract and Tetrahedron Letters, 1992, pp. 3903-3906, vol. 33, No. 27, Chemical Abstract Service, Columbus, Ohio.

Senchenya et al., "Silicon containing esters of alpha-cyanoacrylic acid: synthesis and properties", Database accession No. 123:84703, XP 002248431, abstract and Izvestiya Akademii Nauk, Seriya Khimicheskaya, 1933, pp. 949-952, vol. 5, Chemical Abstract Service, Columbus, Ohio.

Cunningham et al., "Characterisation of a new organosilicon photoresist", Database accession No. 107:246555, XP 002248432, abstract and Proceedings of Spei-the International Society for Optical Engineering (1987), 811 (Opt. Microlithogr. Technol. Integr. Circuit Fabr. Insp.), pp. 186-192, Chemical Abstract Service, Columbus, Ohio.

International Search Report corresponding to PCT EP/03/15038, issued on Jun. 2, 2004, 3 pages.

* cited by examiner

Primary Examiner—Shelley A. Dodson
(74) Attorney, Agent, or Firm—Buchanan, Ingersoll & Rooney, PC

(57) ABSTRACT

Unique photoprotective compositions contain novel methyltrialkylsilanes bearing a cinnamate, cinnamamide, benzalmalonamide or benzalmalonate function, useful as sunscreens that are active in the field of UV radiation.

28 Claims, No Drawings

US 7,354,571 B2

PHOTOPROTECTIVE COMPOSITIONS COMPRISING METHYLTRIALKYLSILANES CONTAINING A CINNAMATE, CINNAMAMIDE, BENZALMALONAMIDE OR BENZALMALONATE FUNCTION

CROSS-REFERENCE TO PRIORITY/PCT/PROVISIONAL APPLICATIONS

This application claims priority under 35 U.S.C. § 119 of FR 03/00909, filed Jan. 28, 2003, and of provisional application Ser. No. 60/450,708, filed Mar. 3, 2003, and is a continuation of PCT/EP 2003/015038, filed Dec. 19, 2003 and designating the United States (published in the English language on Aug. 12, 2004 as WO 2004/067539 A1), each hereby expressly incorporated by reference and each assigned to the assignee hereof.

BACKGROUND OF THE INVENTION

1. Technical Field of the Invention

The present invention relates to novel photoprotective compositions comprising methyltrialkylsilanes containing a cinnamate, cinnamamide, benzalmalonamide or benzalmalonate function, the same being useful as sunscreens that are active in the field of UV radiation.

The present invention also relates to novel methyltrialkylsilanes containing a cinnamate, cinnamamide, benzalmalonamide or benzalmalonate function and to certain applications thereof.

2. Description of Background and/or Related and/or Prior Art

It is known that radiation with wavelengths ranging from 280 nm to 400 nm permits tanning of the human epidermis, and that radiation with wavelengths ranging from 280 to 320 nm, known as UV-B radiation, causes skin burns and erythema that may harm the development of a natural tan. For these reasons, and also for aesthetic reasons, there is an increasing demand for means for controlling this natural tanning. This UV-B radiation should thus be screened out.

It is also known that UV-A rays, with wavelengths ranging from 320 to 400 nm, which cause browning of the skin, are liable to induce impairment in the skin, especially in the case of sensitive skin and/or skin that is continually exposed to sunlight. UV-A rays in particular cause a loss of elasticity of the skin and the appearance of wrinkles, leading to premature aging of the skin. They promote the triggering of the erythemal reaction or amplify this reaction in the case of certain individuals and may even be the cause of phototoxic or photoallergic reactions. Thus, for aesthetic and cosmetic reasons such as conservation of the skin's natural elasticity, more and more individuals wish to control the effect of UV-A rays on their skin. It is thus desirable also to screen out UV-A radiation.

Many organic compounds intended for protecting the skin against UV-A and/or UV-B radiation have been proposed to date.

Most of these are aromatic compounds that absorb UV radiation in the region from 280 nm to 315 nm, or in the region from 315 nm to 400 nm and beyond, or even within both these regions. They are usually formulated in anti-sun or sunscreen compositions that are in the form of oil-in-water or water-in-oil emulsions. The organic screening agents, which are generally lipophilic or hydrophilic, are present in dissolved form, in one or other of these phases, in amounts that are suitable to obtain the desired sun protection factor (SPF).

The "sun protection factor" means the ratio of the irradiation time required to reach the erythema-forming threshold in the presence of the test screening agent, to the radiation time required to reach this same threshold in the absence of screening agent.

Besides their screening power on sunlight, photoprotective compounds must also have good cosmetic properties, good solubility in the usual solvents and in particular in fatty substances such as oils and fats, good resistance to water and to perspiration (remanence) and satisfactory photostability.

Among all of the aromatic compounds that have been recommended for this purpose, mention may be made especially of polysiloxane derivatives containing a benzalmalonate function, described in EP-A-358,584 and in EP-A-392,882 assigned to the assignee hereof. These compounds do indeed have good liposolubility. However, these substances contain very long silicone chains and, on account of their bulk, their synthesis and their incorporation into cosmetic compositions are laborious. Finally, their cosmetic properties are not always satisfactory.

In addition, mention may be made of the silane compounds containing benzalmalonate groups described in EP-A-2,868,905, which describes a process for improving the photostability of dibenzoylmethane derivatives with silane derivatives of benzalmalonates. Mention may also be made of the silane compounds containing benzalmalonate groups described in JP-07-330,779. In this case also, their solubilities in fatty substances and their cosmetic properties are not always satisfactory.

SUMMARY OF THE INVENTION

Novel cinnamate, cinnamamide, benzalmalonamide and benzalmalonate derivatives bearing a methyltrialkylsilane chain have now been developed, these derivatives having very good solubility in fatty substances, improved cosmetic properties (such as the softness of feel) and better absorption (higher E1%).

The present invention thus features cosmetic or dermatological compositions for photoprotecting keratin materials, comprising at least one methyltrialkylsilane compound having the formula (I) below:

in which:

B is a chromophoric group having either of formulae (1) and (2) below:

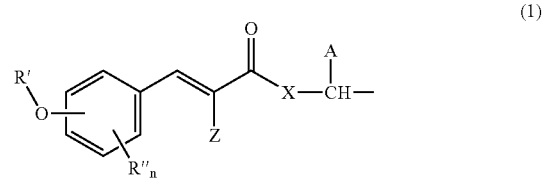

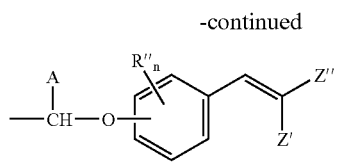

(2)

$R_1$ and $R_2$, which may be identical or different, are each a linear or branched $C_1$-$C_{12}$ alkyl radical, optionally halogenated or containing a double bond or a triple bond, or a phenyl or benzyl radical;

$R_3$ is a radical $R_1$ or $R_2$ or a group B;

n is an integer ranging from 0 to 3 inclusive;

X is —O— or —$NR_5$—;

A is a hydrogen atom, a linear or branched $C_1$-$C_4$ alkyl radical, a group $SiR_1R_2R_3$ in which $R_1$, $R_2$ and $R_3$ are as defined above, with the proviso that $R_3$ is other than B;

the radical R' is a hydrogen atom, a linear or branched $C_1$-$C_{10}$ alkyl radical, a linear or branched $C_2$-$C_8$ alkenyl radical or an $Si(CH_3)_3$ group;

the radicals R", which may be identical or different, are each a hydroxyl radical, a linear or branched $C_1$-$C_{10}$ alkyl radical, a linear or branched $C_2$-$C_8$ alkenyl radical, a linear or branched $C_1$-$C_{10}$ alkoxy radical, with the proviso that R" may together form with an adjacent R" or OR', an alkylidenedioxy group in which the alkylidene group contains one or two carbon atoms, or an —$OSi(CH_3)_3$ group;

Z, Z' and Z", which may be identical or different, are each a hydrogen atom, a linear or branched $C_1$-$C_4$ alkyl radical, a group —(C=O)$R_4$, —(C=O)O$R_4$, —$SO_2R_5$, —(C=O)$NR_6R_7$, —CN or —(C=O)XCHASi$R_1R_2R_3$ in which $R_1$, $R_2$ and $R_3$ are as defined above, with the proviso that $R_3$ is other than B, and with the further proviso that:

(i) at least one of the radicals Z' and Z" is other than hydrogen, and (ii) when Z' is —$SO_2R_5$, then Z" is other than a —CN group;

$R_4$ is a hydrogen atom or a linear or branched $C_1$-$C_{20}$ alkyl radical;

$R_5$ is a $C_1$-$C_{20}$ alkyl radical or a $C_6$-$C_{12}$ aryl radical;

$R_6$ and $R_7$, which may be identical or different, are each a hydrogen atom or a $C_1$-$C_4$ alkyl radical; with the further proviso that:

Z' and Z" may also together form a Meldrum acid of formula (3) below:

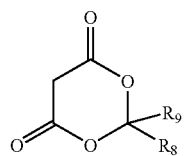

(3)

in which $R_8$ and $R_9$, which may be identical or different, are each hydrogen or a linear or branched $C_1$-$C_{20}$ alkyl radical, and $R_8$ and $R_9$ may also together form a $C_5$-$C_{12}$ ring member.

DETAILED DESCRIPTION OF BEST MODE AND SPECIFIC/PREFERRED EMBODIMENTS OF THE INVENTION

Although, in formula (I) above in which the substituents are different, only one isomer is depicted, this formula should be understood as also including the corresponding trans isomers.

In formula (I) above, the alkyl radicals may be linear or branched, saturated or unsaturated, and selected especially from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The alkyl radical that is particularly preferred is the methyl radical.

In formula (I) above, the alkoxy radicals may be linear or branched and selected especially from among methoxy, ethoxy, n-propoxy, isopropoxy, n-butoxy and isobutoxy radicals. The alkoxy radical that is particularly preferred is the methoxy radical.

In formula (I) above, the alkenyl radicals may be linear or branched and selected especially from among ethylene, propylene and butene radicals.

In formula (I) above, the aryl radicals are preferably phenyl or benzyl radicals.

Among the compounds of formula (I) in which B corresponds to formula (1), mention will be made more particularly of those for which:

$R_1$, $R_2$ and $R_3$ is a $C_1$-$C_4$ alkyl and more particularly simultaneously methyl;

Z is hydrogen, COO$R_4$ in which $R_4$ is a $C_1$-$C_8$ alkyl and more particularly methyl, CN or —(C=O)XCHASi$R_1R_2R_3$;

A is a hydrogen atom;

X is O or NH;

n=0;

R' is a $C_1$-$C_4$ alkyl radical and more particularly methyl.

Among these compounds, mention may be made even more particularly of the following compounds:

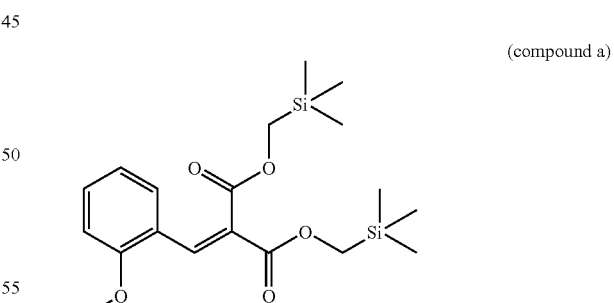

(compound a)

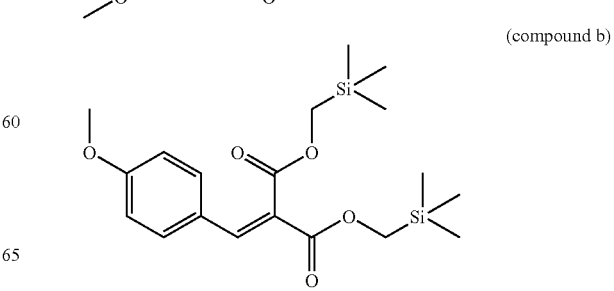

(compound b)

-continued (compound c)
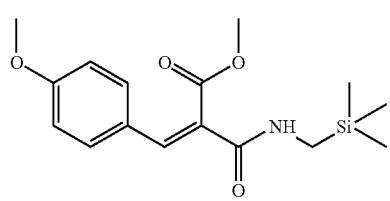

(compound d)
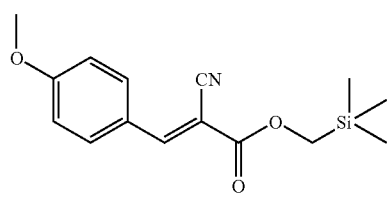

(compound e)
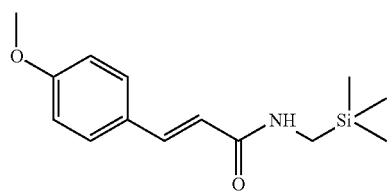

(compound f)
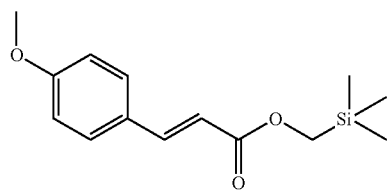

Among the compounds of formula (I) in which B corresponds to formula (2), mention will be made more particularly of those for which:

$R_1$ and $R_2$ is a $C_1$-$C_4$ alkyl and more particularly methyl;
n=0 or 1 with, when n=1, R" is a $C_1$-$C_4$ alkoxy radical and more particularly methoxy;
A is a hydrogen atom;
Z' and Z", which may be identical or different, are each a group selected from:
1) —(C=O)O$R_4$ in which $R_4$ is a $C_1$-$C_8$ alkyl and more particularly methyl, ethyl, isobutyl or 2-ethylhexyl;
2) —(C=O)NH$_2$;
3) —CN;
4) a group of formula (3) in which $R_8$ and $R_9$ is a $C_1$-$C_4$ alkyl and more particularly methyl.

Among these compounds, mention may be made more particularly of the following compounds:

(compound g)
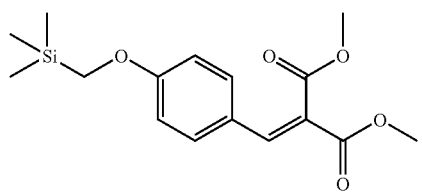

-continued (compound h)
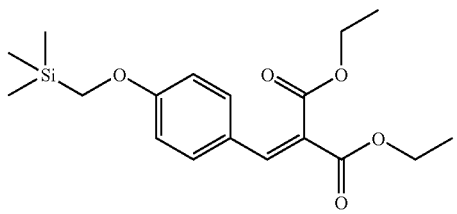

(compound i)
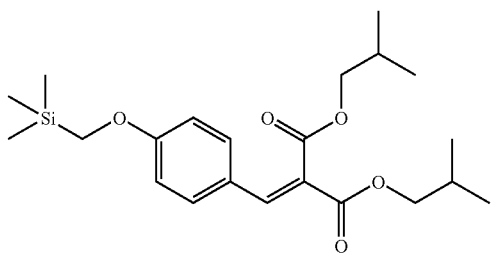

(compound j)
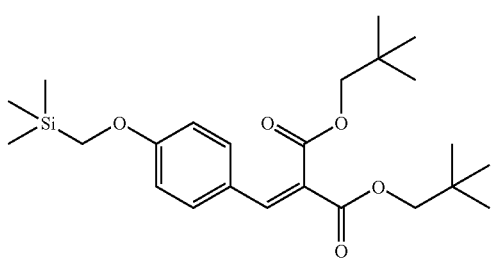

(compound k)
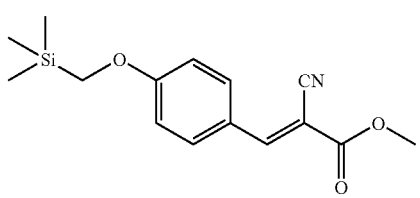

(compound l)
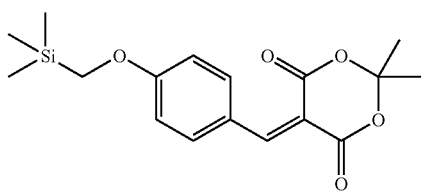

(compound m)
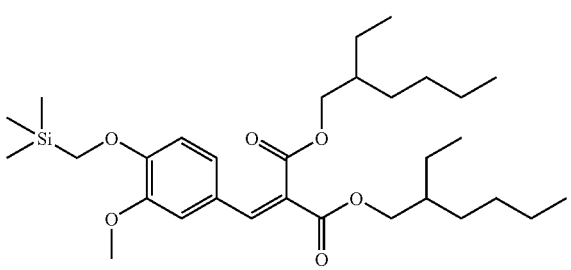

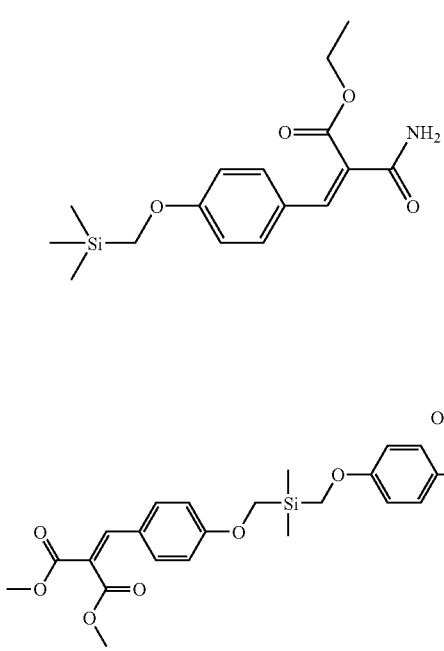

(compound n)

(compound o)

(compound p)

(compound q)

The compounds of formula (I) according to the invention are novel, with the exception of trimethylsilanylmethyl 2-cyano-3-(4-methoxyphenyl)acrylic acid (compound (d) as described above; RN: 165552-16-9) described in the article N. G. Senchenya et al., *Tzvestiya Akademii Nauk, Seriva Khimicheskaya*, 5, 949-52 (1993).

To prepare the silane compounds in accordance with the invention of formula (I) in which the chromophoric group B is of formula (2), one of the following two methods may be used:

Route A:

An aromatic hydroxybenzaldehyde of formula (4) below is reacted with a monohalo or dihalo methylsilane derivative in the presence of a base (standard alkylation reaction), the benzaldehyde obtained being condensed with a difunctional compound Z'-CH$_2$-Z" in toluene in the presence of piperidinium acetate as catalyst (Knoevenagel condensation) according to the following scheme:

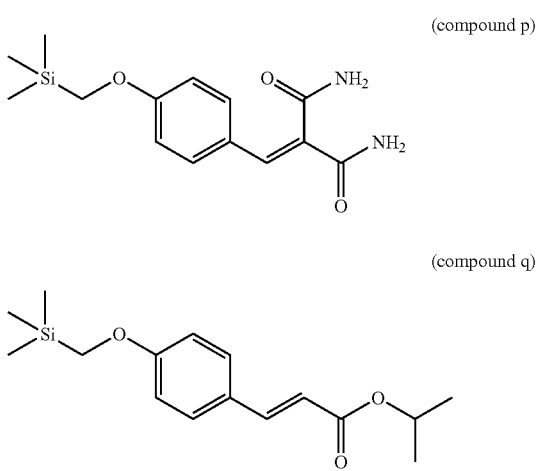

in which p is 1 or 2; Y is Hal or $R_2$ or $R_1$; R", n, $R_1$ to $R_3$, A, Z' and Z" have the meanings given above for formula (I) and Hal represents a halogen and more particularly chlorine.

Route B:

This entails reacting a derivative of formula (6) below with a monohalo or dihalo methylsilane derivative of formula (5) in the presence of a base (standard alkylation reaction):

in which Y, Hal, R", p, m, $R_1$ to $R_3$, A, Z' and Z" have the meanings given above for route A.

Aromatic benzaldehyde derivatives of formula (4) that may be mentioned include 4-hydroxybenzaldehyde and vanillin, which are commercial products.

Derivatives of Z'-CH$_2$-Z" type that may be mentioned include dimethyl malonate and diethyl malonate, which are commercial products.

A derivative of formula (6) that may be mentioned is dimethyl para-hydroxybenzalmalonate sold by Acros.

Silane halide derivatives of formula (5) that may be mentioned include chloromethyltrimethylsilane (RN 2344-80-1) and bis(chloromethyl)dimethylsilane (RN 2917-46-6), sold by Wacker. Mention may also be made of the following commercial products:
(chloromethyl)dimethylethylsilane (RN 3121-77-5),
(chloromethyl)dimethyl-n-butylsilane (RN 3121-75-3),
(chloromethyl)dimethylpentylsilane (RN 73013-39-5),
(chloromethyl)dodecyidimethylsilane (RN 70851-47-7), (chloromethyl)triethylsilane (RN 757-34-6),
2-chloroethyltrimethylsilane (RN 7787-87-3),
bis(trimethylsilyl)methyl chloride (RN 5926-35-2),
(chloromethyl)dimethylphenylsilane (RN 1833-51-8),
(chloromethyl)diphenylmethylsilane (RN 18407-40-4) and
(trimethylsilylmethyl)dimethylchloromethylsilane (RN 18306-73-5).

To prepare the silane compounds in accordance with the invention of formula (I) in which the chromophoric group B is of formula (1), the method of condensing the benzaldehyde of formula (6) with the compound of formula (7) in toluene in the presence of piperidinium acetate as catalyst (Knoevenagel condensation) may be used, according to the following scheme:

Route C:

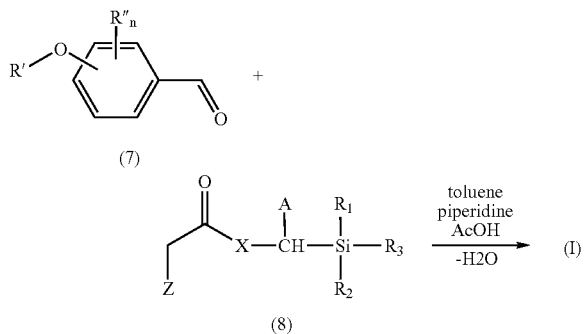

in which R', R", n, A, $R_1$ to $R_3$, Z and X have the meanings given above for formula (I), the compounds of formula (8) themselves possibly being obtained, depending on whether X is —O— or —$NR_5$—, according to the following methods:

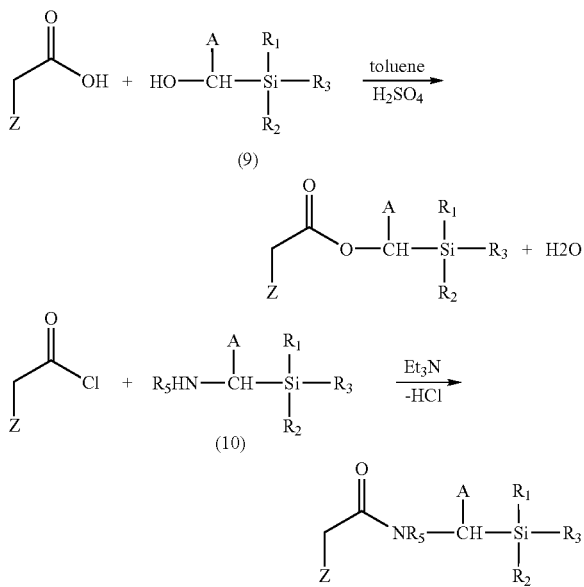

in which Z, A, $R_1$ to $R_3$ and $R_5$ have the meanings given above for formula (1).

Aromatic benzaldehyde derivatives of formula (7) that may be mentioned include 4-methoxybenzaldehyde, veratraldehyde and piperonal, which are commercial products.

Derivatives of Z'-$CH_2$—COOH type that may be mentioned include cyanoacetic acid, monoethyl malonate and mono-tert-butyl malonate, which are commercial products.

A derivative of Z'-$CH_2$COCl type that may be mentioned is monoethyl malonate acid chloride, which is a commercial product.

Derivatives of formulae (9) and (10) that may be mentioned include hydroxymethyltrimethylsilane and aminomethyltrimethylsilane, sold by Gelest, and bis(trimethylsilyl)methylamine (RN 134340-00-4).

The compounds of formula (I) are generally present in the composition of the invention in proportions ranging from 0.01% to 20% by weight and preferably from 0.1% to 10% by weight relative to the total weight of the composition.

The compositions in accordance with the invention may also comprise other additional UV-A-active and/or UV-B-active organic or mineral UV-screening agents, which are water-soluble or liposoluble or even insoluble in the cosmetic solvents commonly used.

The additional organic screening agents are selected especially from anthranilates; cinnamic derivatives; dibenzoylmethane derivatives; salicylic derivatives; camphor derivatives; triazine derivatives such as those described in U.S. Pat. No. 4,367,390, EP-863,145, EP-517,104, EP-570,838, EP-796,851, EP-775,698, EP-878,469, EP-933,376, EP-507,691, EP-507,692, EP-790,243, EP-944,624; benzophenone derivatives; β,β-diphenylacrylate derivatives; benzotriazole derivatives; benzalmalonate derivatives; benzimidazole derivatives; imidazolines; bis-benzazolyl derivatives as described in EP-669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB-2,303, 549, DE-197,26,184 and EP-893,119; benzoxazole derivatives as described in EP-0,832,642, EP-1,027,883, EP-1,300,137 and DE-101,62,844; screening polymers and screening silicones such as those described especially in WO 93/04665; dimers derived from α-alkylstyrene, such as those described in DE-198,55,649; 4,4-diarylbutadienes such as those described in EP-0,967,200, DE-197,46,654, DE-197,55,649, EP-A-1,008,586, EP-1,133,980 and EP-133,981, and mixtures thereof.

As examples of additional organic screening agents, mention may be made of those denoted hereinbelow under their INCI name:

para-Aminobenzoic Acid Derivatives:
PABA,
Ethyl PABA,
Ethyl dihydroxypropyl PABA,
Ethylhexyl dimethyl PABA sold in particular under the name "Escalol 507" by
ISP,
Glyceryl PABA,
PEG-25 PABA sold under the name "Uvinul P25" by BASF.

Salicylic Derivatives:
Homosalate sold under the name "Eusolex HMS" by Rona/EM Industries,
Ethylhexyl salicylate sold under the name "Neo Heliopan OS" by Haarmann and Reimer,
Dipropylene glycol salicylate sold under the name "Dipsal" by Scher,
TEA salicylate sold under the name "Neo Heliopan TS" by Haarmann and Reimer.

Dibenzoylmethane Derivatives:
Butyl methoxydibenzoylmethane sold in particular under the trademark "Parsol 1789" by Hoffmann LaRoche,
Isopropyldibenzoylmethane.

Cinnamic Derivatives:
Ethylhexyl methoxycinnamate sold in particular under the trademark "Parsol MCX" by Hoffmann LaRoche,
Isopropyl methoxycinnamate,
Isoamyl methoxycinnamate sold under the trademark "Neo Heliopan E 1000" by Haarmann and Reimer,
Cinoxate,
DEA methoxycinnamate,
Diisopropyl methylcinnamate,
Glyceryl ethylhexanoate dimethoxycinnamate.
β,β'-Diphenylacrylate Derivatives:
Octocrylene sold in particular under the trademark "Uvinul N539" by BASF,
Etocrylene sold in particular under the trademark "Uvinul N35" by BASF.
Benzophenone Derivatives:
Benzophenone-1 sold under the trademark "Uvinul 400" by BASF,
Benzophenone-2 sold under the trademark "Uvinul D50" by BASF,
Benzophenone-3 or Oxybenzone sold under the trademark "Uvinul M40" by
BASF,
Benzophenone-4 sold under the trademark "Uvinul MS40" by BASF,
Benzophenone-5,
Benzophenone-6 sold under the trademark "Helisorb 11" by Norquay,
Benzophenone-8 sold under the trademark "Spectra-Sorb UV-24" by American Cyanamid,
Benzophenone-9 sold under the trademark "Uvinul DS-49" by BASF,
Benzophenone-12
n-hexyl 2-(4-diethylamino-2-hydroxybenzoyl)benzoate.
Benzylidenecamphor Derivatives:
3-Benzylidenecamphor manufactured under the name "Mexoryl SD" by Chimex,
4-Methylbenzylidenecamphor sold under the name "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.
Phenylbenzimidazole Derivatives:
Phenylbenzimidazolesulfonic acid sold in particular under the trademark "Eusolex 232" by Merck,
Disodium phenyl dibenzimidazole tetrasulfonate, sold under the trademark "Neo Heliopan AP" by Haarmann and Reimer.
Triazine Derivatives:
Anisotriazine sold under the trademark "Tinosorb S" by Ciba Geigy,
Ethylhexyltriazone sold in particular under the trademark "Uvinul T150" by BASF,
2,4,6-tris(diisobutyl 4'-aminobenzalmalonate)-s-triazine,
Diethylhexylbutamidotriazone sold under the trademark "Uvasorb HEB" by Sigma 3V.
Phenylbenzotriazole Derivatives:
Drometrizole trisiloxane sold under the name "Silatrizole" by Rhodia Chimie,
Methylenebis(benzotriazolyl)tetramethylbutylphenol sold in solid form under the trademark "MIXXIM BB/100" by Fairmount Chemical, or in micronized form as an aqueous dispersion under the trademark "Tinosorb M" by Ciba Specialty Chemicals.
Anthranilic Derivatives:
Menthyl anthranilate sold under the trademark "Neo Heliopan MA" by Haarmann and Reimer.
Imidazoline derivatives:
Ethylhexyldimethoxybenzylidenedioxoimidazoline propionate.
Benzalmalonate derivatives:
Polyorganosiloxane containing benzalmalonate functions, such as the product Polysilicone-15 sold under the trademark "Parsol SLX" by Hoffmann LaRoche
4,4-Diarylbutadiene Derivatives:
1,1-Dicarboxy(2,2'-dimethylpropyl)-4,4-diphenylbutadiene
Benzoxazole Derivatives:
2,4-bis[5-1 (dimethylpropyl)benzoxazol-2-yl(4-phenyl)imino]-6-(2-ethylhexyl)imino-1,3,5-triazine, sold under the name Uvasorb K2A by Sigma 3V, and mixtures thereof.

The preferred additional organic UV-screening agents are selected from:
Ethylhexyl salicylate,
Ethylhexyl methoxycinnamate,
Butyl methoxydibenzoylmethane,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
2,4,6-Tris(diisobutyl 4'-aminobenzalmalonate)-s-triazine,
Anisotriazine,
Ethylhexyltriazone,
Diethylhexylbutamidotriazone,
Methylenebis(benzotriazolyl)tetramethylbutylphenol,
Drometrizole trisiloxane,
Polysilicone-15
1,1-Dicarboxy(2,2'-dimethylpropyl)-4,4-diphenylbutadiene,
2,4-bis[5-1 (dimethylpropyl)benzoxazol-2-yl(4-phenyl)imino]-6-(2-ethylhexyl)imino-1,3,5-triazine and mixtures thereof.

The additional mineral screening agents are selected from pigments or nanopigments (mean size of the primary particles: generally from 5 nm to 100 nm and preferably from 10 nm to 50 nm) of coated or uncoated metal oxides such as, for example, nanopigments of titanium oxide (amorphous or crystallized in rutile and/or anatase form), of iron oxide, of zinc oxide, of zirconium oxide or of cerium oxide, which are all UV photoprotective agents that are well known per se. Standard coating agents are, moreover, alumina and/or aluminum stearate. Such coated or uncoated metal oxide nanopigments are described in particular in EP-518,772 and EP-518,773.

The additional UV-screening agents in accordance with the invention are generally present in the compositions according to the invention in proportions ranging from 0.01% to 20% by weight relative to the total weight of the composition, and preferably ranging from 0.1% to 10% by weight relative to the total weight of the composition.

The cosmetic compositions according to the invention may also contain agents for artificially tanning and/or browning the skin (self-tanning agents) such as dihydroxyacetone (DHA).

The compositions in accordance with the present invention may also comprise standard cosmetic adjuvants selected especially from fatty substances, organic solvents, ionic or nonionic thickeners, softeners, humectants, antioxidants, moisturizers, desquamating agents, free-radical scavengers, anti-pollution agents, anti-bacterial agents, anti-inflammatory agents, depigmenting agents, propigmenting agents, opacifiers, stabilizers, emollients, silicones, anti-foams, insect repellents, fragrances, preservatives, anionic, cationic, nonionic, zwitterionic or amphoteric surfactants, substance P antagonists, substance CGRP antagonists, fillers, pigments, polymers, propellants, acidifying or basifying agents, or any other ingredient usually used in cosmetics and/or dermatology.

The fatty substances may consist of an oil or a wax or mixtures thereof. The term "oil" means a compound that is liquid at room temperature. The term "wax" means a compound that is solid or substantially solid at room temperature, and whose melting point is generally above 35° C.

Oils that may be mentioned include mineral oils (paraffin); plant oils (sweet almond oil, macadamia oil, blackcurrant seed oil or jojoba oil); synthetic oils, for instance perhydrosqualene, fatty alcohols, fatty acids or fatty acid esters (for instance the C12-C15 alcohol benzoate sold under the trademark "Finsolv TN" by Witco, octyl palmitate, isopropyl lanolate, triglycerides, including capric/caprylic acid triglycerides), oxyethylenated or oxypropylenated fatty esters and ethers; silicone oils (cyclomethicone and polydimethylsiloxanes, or PDMS) or fluoro oils, and polyalkylenes.

Waxy compounds that may be mentioned include paraffin, carnauba wax, beeswax and hydrogenated castor oil.

Among the organic solvents that may be mentioned are lower alcohols and polyols. These solvents may be selected from glycols and glycol ethers, for instance ethylene glycol, propylene glycol, butylene glycol, dipropylene glycol or diethylene glycol.

The thickeners may be selected especially from crosslinked acrylic polymers, for instance Carbomers, crosslinked polymer acrylates/C10-C30 alkylacrylate crosslinked polymers of the type such as Pemulen or poly-acrylate-3 sold under the name Viscophobe DB 1000 by Amerchol; poly-acrylamides such as the emulsion of poly-acrylamide, C13-C14 isoparaffin and laureth-7 sold under the name Sepigel 305 by SEPPIC, AMPS homopolymers or copolymers such as Hostacerin AMPS sold by Clariant, modified or unmodified guar gums and celluloses, such as hydroxypropyl guar gum, methylhydroxyethylcellulose and hydroxypropylmethyl cellulose, xanthan gum, and nanometric silicas of the Aerosil type.

Needless to say, one skilled in the art will take care to select the optional additional compound(s) mentioned above and/or the amounts thereof such that the advantageous properties intrinsically associated with the compositions in accordance with the invention are not, or are not substantially, adversely affected by the envisaged addition(s).

The compositions according to the invention may be prepared according to techniques that are well known to those skilled in the art, in particular those intended for the preparation of emulsions of oil-in-water or water-in-oil type.

This composition may be in particular in the form of a simple or complex emulsion (O/W, W/O, O/W/O or W/O/W emulsion) such as a cream or a milk, in the form of a gel or a cream-gel, or in the form of a lotion, an oil, a powder or a solid tube, and may optionally be packaged as an aerosol and may be in the form of a mousse or a spray.

The compositions according to the invention are preferably in the form of an oil-in-water or water-in-oil emulsion.

When it is an emulsion, the aqueous phase of this emulsion may comprise a nonionic vesicular dispersion prepared according to known processes (Bangham, Standish and Watkins, *J. Mol. Biol.*, 13, 238 (1965), FR-2,315,991 and FR-2,416,008).

When the cosmetic composition according to the invention is used to care for the human epidermis, it may be in the form of a suspension or a dispersion in solvents or fatty substances, in the form of a nonionic vesicular dispersion or in the form of an emulsion, preferably of oil-in-water type, such as a cream or a milk, or in the form of an ointment, a gel, a cream-gel, an anti-sun oil, a solid tube, a powder, an aerosol mousse or a spray.

When the cosmetic composition according to the invention is used for haircare, it may be in the form of a shampoo, a lotion, a gel, an emulsion or a nonionic vesicular dispersion and may constitute, for example, a rinse-out composition, to be applied before or after shampooing, before or after dyeing or bleaching, or before, during or after permanent-waving or relaxing the hair, a styling or treating lotion or gel, a blow-drying or hairsetting lotion or gel, or a composition for permanent-waving, relaxing, dyeing or bleaching the hair.

When the composition is used as a makeup product for the nails, the lips, the eyelashes, the eyebrows or the skin, such as an epidermal treatment cream, a foundation, a tube of lipstick, an eyeshadow, a makeup rouge, a mascara or an eyeliner, it may be in solid or pasty, anhydrous or aqueous form, such as oil-in-water or water-in-oil emulsions, non-ionic vesicular dispersions or suspensions.

As a guide, for the anti-sun or sunscreen formulations in accordance with the invention which contain a support of oil-in-water emulsion type, the aqueous phase (especially comprising the hydrophilic screening agents) generally represents from 50% to 95% by weight and preferably from 70% to 90% by weight relative to the total weight of the formulation, the oily phase (especially comprising the lipophilic screening agents) generally represents from 5% to 50% by weight and preferably from 10% to 30% by weight relative to the total weight of the formulation, and the (co)-emulsifier(s) generally represent(s) from 0.5% to 20% by weight and preferably from 2% to 10% by weight relative to the total weight of the formulation.

This invention also features the formulation of a compound of formula (I) as defined above in a cosmetic or dermatological composition, as an agent for screening out UV radiation.

The present invention also features administration of a compound of formula (I) as defined above in a cosmetic composition, as an agent in a regime or regimen for controlling the variation in the color of the skin caused by UV radiation.

The present invention also features using a compound of formula (I) as defined above as an agent for photostabilizing synthetic polymers such as plastics or glasses, in particular spectacle glasses or contact lenses.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Synthesis of dimethyl 2-(4-trimethylsilanylmethoxy)benzylidenemalonate According to Route A

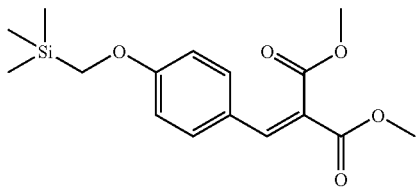

a) First Step: Preparation of 4-trimethylsilanylmethoxybenzaldehyde:

Chloromethyltrimethylsilane (110.5 g, 0.9 mol) is added dropwise over 30 minutes to a mixture of para-hydroxybenzaldehyde (110 g, 0.82 mol) and potassium carbonate (124.5 g, 0.9 mol) in 1 L of dry DMF maintained at 80° C., and while sparging with nitrogen. The mixture is left at 90° C. for 4 hours. The reaction mixture is filtered and the solvent is removed from the filtrate by distillation under vacuum. The final traces of DMF are removed via a stage at 60° C. under a vacuum of 2 mmHg. 142.4 g (yield: 84%) of 4-trimethylsilanylmethoxybenzaldehyde are obtained in the form of an orange-yellow oil, which is used without further purification in the next step.

b) Second Step: Synthesis of the Derivative of Example 1:

A mixture of the above derivative (75 g, 0.36 mol) and dimethyl malonate (52.3 g, 0.396 mol) in 120 ml of toluene in the presence of 3.6 ml of piperidine and 2.2 ml of acetic acid is refluxed for 5 hours in a reactor equipped with Dean-Stark apparatus. The water formed is removed azeotropically. The mixture is cooled and the toluene is removed by distillation. The reaction mixture is taken up in 400 ml of diisopropyl ether. The organic phase is washed 3 times with water, dried over sodium sulfate and filtered, and the solvent is evaporated off under vacuum. The orange-colored oil obtained (110.3 g) is purified by chromatography on a column of silica (eluent: 95/5 heptane/EtOAc). 47 g of clean fractions (yield: 40%) of the derivative of Example 1 are recovered in the form of a pale yellow viscous oil:

| UV (ethanol) | $\lambda_{max}$ = 317 nm, | $\epsilon_{max}$ = 27 085, | $E_{1\%}$ = 840. |

EXAMPLE 2

Synthesis of dimethyl 2-(4-trimethylsilanylmethoxy)benzylidenemalonate According to Route B

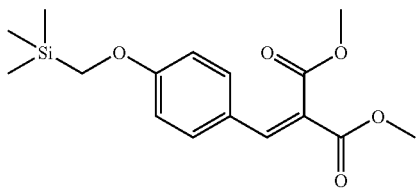

Chloromethyltrimethylsilane (9.5 ml, 0.068 mol) is added dropwise over 30 minutes to a mixture of dimethyl para-hydroxybenzalmalonate (15 g, 0.056 mol) and potassium carbonate (9.4 g, 0.068 mol) in 60 ml of dry DMF maintained at 80° C., and while sparging with nitrogen. The mixture is left at 120° C. for 2 hours. The reaction mixture is cooled and poured into ice-cold water. The oily phase is extracted with dichloromethane. The organic phase is washed 3 times with water, dried over sodium sulfate and filtered, and the solvent is evaporated off under vacuum. The final traces of DMF are removed via a stage at 60° C. under a vacuum of 2 mmHg. The brown oil obtained is purified by chromatography on a column of silica (eluent: 95/5 heptane/EtOAc). 7.1 g of clean fractions (yield: 36%) of the derivative of Example 2 are recovered in the form of a pale yellow viscous oil:

| UV (ethanol) | $\lambda_{max}$ = 317 nm, | $\epsilon_{max}$ = 26 440, | $E_{1\%}$ = 820. |

EXAMPLE 3

Synthesis of diethyl 2-(4-trimethylsilanylmethoxy)benzylidenemalonate According to Route B

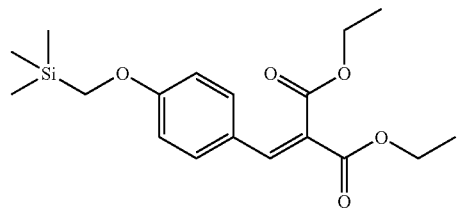

Chloromethyltrimethylsilane (9.5 ml, 0.068 mol) is added dropwise over 30 minutes to a mixture of diethyl para-hydroxybenzalmalonate (15 g, 0.056 mol) and potassium carbonate (9.4 g, 0.068 mol) in 60 ml of dry DMF maintained at 80° C., and while sparging with nitrogen. The mixture is left at 120° C. for 2 hours. The reaction mixture is cooled and poured into ice-cold water. The oily phase is extracted with dichloromethane. The organic phase is washed 3 times with water, dried over sodium sulfate and filtered, and the solvent is evaporated off under vacuum. The final traces of DMF are removed via a stage at 60° C. under a vacuum of 2 mmHg. The brown oil obtained is purified by chromatography on a column of silica (eluent: 95/5 heptane/EtOAc). 7.1 g of clean fractions (yield: 36%) of the derivative of Example 3 are recovered in the form of a pale yellow viscous oil:

| UV (ethanol) | $\lambda_{max}$ = 316 nm, | $\epsilon_{max}$ = 26 290, | $E_{1\%}$ = 750. |

EXAMPLE 4

Synthesis of diisobutyl 2-(4-trimethylsilanylmethoxy)benzylidenemalonate According to Route A

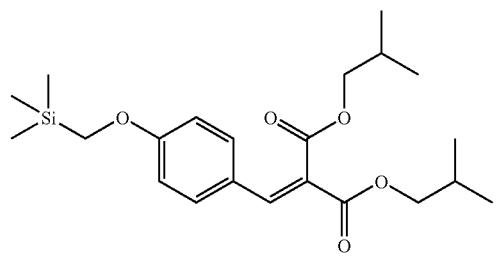

4-(Trimethylsilanylmethoxy)benzaldehyde (obtained in step 1 of Example 1) (4.35 g, 0.02 mol) and diisobutyl malonate (5.13 ml, 0.022 mol) in 10 ml of dry toluene in the presence of 0.21 ml of piperidine and 0.13 g of acetic acid is refluxed for 5 hours in a reactor equipped with Dean-Stark apparatus. The water formed is removed azeotropically. The mixture is cooled and the toluene is removed by distillation. The reaction mixture is taken up in 50 ml of diisopropyl ether. The organic phase is washed 3 times with water, dried over sodium sulfate and filtered, and the solvent is evaporated off under vacuum. The brown oil obtained (8.4 g) is purified by chromatography on a column of silica (eluent: 90/10 heptane/EtOAc). 3.82 g of clean fractions (yield: 45%) of the derivative of Example 4 are recovered in the form of a colorless viscous oil:

UV (ethanol)   $\lambda_{max}$ = 316 nm,   $\epsilon_{max}$ = 26 960,   $E_{1\%}$ = 663.

EXAMPLE 5

Synthesis of dineopentyl 2-(4-trimethylsilanylmethoxy)benzylidenemalonate According to Route A

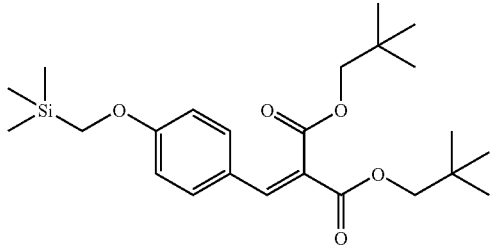

a) First Step: Preparation of dineopentyl malonate:

Malonic acid (40 g, 0.38 mol) and neopentyl alcohol (77.5 g, 0.88 mol) in 110 ml of toluene in the presence of 0.2 ml of concentrated sulfuric acid are refluxed for 3 hours in a reactor equipped with Dean-Stark apparatus. The water formed is removed azeotropically. The organic phase is washed 3 times with water and dried over sodium sulfate. After filtration and evaporation of the solvent under vacuum, 88 g (yield: 94%) of dineopentyl malonate are obtained in the form of a colorless oil and used without further purification in the next step.

b) Second Step: Synthesis of the Derivative of Example 5:

4-(Trimethylsilanylmethoxy)benzaldehyde (obtained in step 1 of Example 1) (2 g, 9.6×10$^{-3}$ mol) and dineopentyl malonate (2.6 g, 10.6×10$^{-3}$ mol) in 10 ml of dry toluene in the presence of 8 mg of piperidine and 6 mg of acetic acid are refluxed for 5 hours in a reactor equipped with Dean-Stark apparatus. The water formed is removed azeotropically. The mixture is cooled and the toluene is removed by distillation. The reaction mixture is taken up in 50 ml of diisopropyl ether. The organic phase is washed 3 times with water, dried over sodium sulfate and filtered, and the solvent is evaporated off under vacuum. The brown oil obtained (4 g) is purified by chromatography on a column of silica (eluent: 95/5 heptane/EtOAc). 2.5 g of clean fractions (yield: 60%) of the derivative of Example 5 are recovered in the form of a colorless viscous oil. This oil crystallizes over time to give translucent crystals:

m.p. 60° C.
UV (ethanol)   $\lambda_{max}$ = 317 nm,   $\epsilon_{max}$ = 25 730,   $E_{1\%}$ = 592.

EXAMPLE 6

Synthesis of 2,2-dimethyl-5-[4-(trimethylsilanylmethoxy)benzylidene]-1,3-dioxane-4,6-dione According to Route A

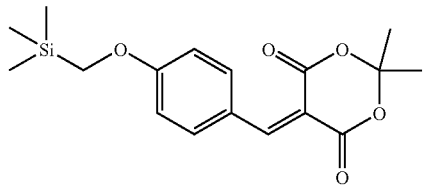

4-(Trimethylsilanylmethoxy)benzaldehyde (obtained in step 1 of Example 1) (5 g, 0.024 mol) and isopropylidenemalonate (3.8 g, 0.0264 mol) in 10 ml of dry toluene in the presence of 0.24 ml of piperidine and 0.14 g of acetic acid are refluxed for 5 hours in a reactor equipped with Dean-Stark apparatus. The water formed is removed azeotropically. The mixture is cooled and the toluene is removed by distillation. The reaction mixture is taken up in 50 ml of diisopropyl ether. The organic phase is washed 3 times with water, dried over sodium sulfate and filtered, and the solvent is evaporated off under vacuum. The yellow oil obtained (7.48 g) is purified by chromatography on a column of silica (eluent: 95/5 heptane/EtOAc). 3.64 g of clean fractions (yield; 45% of the derivative of Example 6 are recovered in the form of a yellow solid:

m.p. 84-86° C.
UV (ethanol)   $\lambda_{max}$ = 370 nm,   $\epsilon_{max}$ = 25 230,   $E_{1\%}$ = 756.

EXAMPLE 7

Synthesis reparation of bis(2-ethylhexyl) 2-[3-methoxy-4-(trimethylsilanylmethoxy)benzylidene]malonate According to Route A

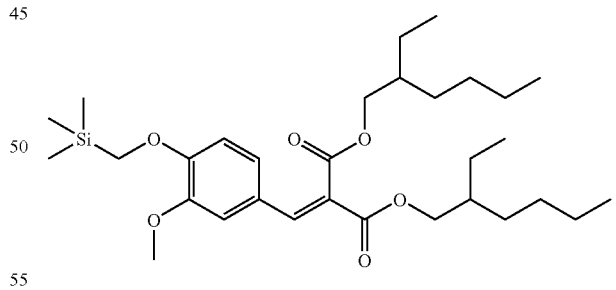

a) First Step: Preparation of 3-methoxy-4-trimethylsilanylmethoxybenzaldehyde:

Chloromethyltrimethylsilane (36.7 g, 0.3 mol) is added dropwise over 10 minutes to a mixture of vanillin (45.6 g, 0.3 mol) and potassium carbonate (41.4 g, 0.3 mol) in 300 ml of dry DMF maintained at 100° C., and while sparging with nitrogen. The mixture is left at 100° C. for 2 hours. The reaction mixture is filtered and the solvent is removed from the filtrate by distillation under vacuum. The final traces of DMF are removed via a stage at 60° C. under a vacuum of 2 mmHg. 70 g of a pink syrup, which crystallizes, are obtained. After recrystallization from an 80/20 ethanol/water mixture, 35.5 g (yield: 50%) of 3-methoxy-4-trimethylsilanylmethoxybenzaldehyde are obtained in the form of white crystals (m.p. 45° C.), which are used without purification in the next step.

b) Second Step: Synthesis of the Derivative of Example 7:

4-(Trimethylsilanylmethoxy)benzaldehyde (obtained in step 1 of Example 1) (5 g, 0.024 mol) and the derivative from the preceding step (7.6 g, 0.024 mol) in 10 ml of dry toluene in the presence of 0.24 ml of piperidine and 0.14 g of acetic acid are refluxed for 5 hours in a reactor equipped with Dean-Stark apparatus. The water formed is removed azeotropically. The mixture is cooled and the toluene is removed by distillation. The reaction mixture is taken up in 50 ml of diisopropyl ether. The organic phase is washed 3 times with water, dried over sodium sulfate and filtered, and the solvent is evaporated off under vacuum. The yellow oil obtained is purified by chromatography on a column of silica (eluent: 99/1 heptane/EtOAc). 7.8 g of clean fractions (yield: 68%) of the derivative of Example 7 are recovered in the form of a pale yellow oil:

| UV (ethanol) | $\lambda_{max}$ = 331 nm, | $\epsilon_{max}$ = 18 170, | $E_{1\%}$ = 331. |
|---|---|---|---|

EXAMPLE 8

Synthesis of ethyl 2-(aminocarbonyl)-3-[4-(trimethylsilanylmethoxy)phenyl]acrylate According to Route A

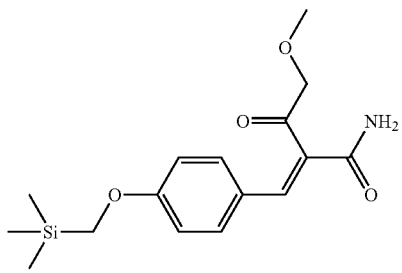

4-(Trimethylsilanylmethoxy)benzaldehyde (obtained in step 1 of Example 1) (3 g, 0.015 mol) and ethyl malonate monoamide (2.1 g, 0.016 mol) in 10 ml of dry toluene in the presence of 0.24 ml of piperidine and 0.14 g of acetic acid are refluxed for 3 hours in a reactor equipped with Dean-Stark apparatus. The water formed is removed azeotropically. The mixture is cooled and the toluene is removed by distillation. The reaction mixture is taken up in 50 ml of diisopropyl ether. The organic phase is washed 3 times with water, dried over sodium sulfate and filtered, and the solvent is evaporated off under vacuum. The yellow gum obtained is crystallized from a diisopropyl ether/heptane mixture. 1.8 g (yield: 37%) of the derivative of Example 8 are obtained in the form of a pale yellow solid:

| m.p. 77-8° C. | | | |
|---|---|---|---|
| UV (ethanol) | $\lambda_{max}$ = 314 nm, | $\epsilon_{max}$ = 24 270, | $E_{1\%}$ = 755. |

EXAMPLE 9

Synthesis of dimethyl 2-(4-{[({4-[3-methoxy-2-(methoxycarbonyl)-3-oxoprop-1-enyl]phenoxy}methyl)(dimethyl)silyl]methoxy}benzylidene)malonate According to Route B

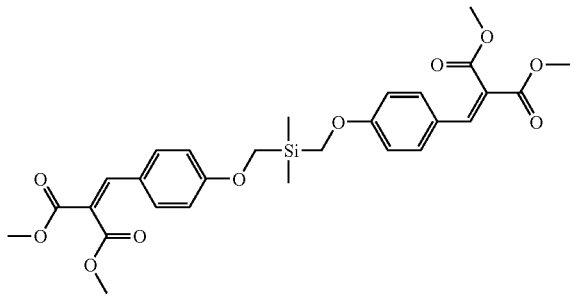

Bis(chloromethyl)dimethylsilane (1.53 ml, 0.0105 mol) is added dropwise over 30 minutes to a mixture of dimethyl para-hydroxybenzalmalonate (5 g, 0.021 mol) and potassium carbonate (2.9 g, 0.021 mol) in 15 ml of dry DMF maintained at 60° C., and while sparging with nitrogen. The mixture is left at 60° C. for 2 hours. The reaction mixture is cooled and poured into ice-cold water. The oily phase is extracted with dichloromethane. The organic phase is washed 3 times with water, dried over sodium sulfate and filtered, and the solvent is evaporated off under vacuum. The final traces of DMF are removed via a stage at 60° C. under a vacuum of 2 mmHg. The solid obtained is recrystallized from a 90/10 ethanol/water mixture. 5.2 g (yield: 88%) of the derivative of Example 9 are obtained in the form of a pale beige solid:

| m.p. 103-104° C. | | | |
|---|---|---|---|
| UV (ethanol) | $\lambda_{max}$ = 316 nm, | $\epsilon_{max}$ = 50 270, | $E_{1\%}$ = 903. |

EXAMPLE 10

Synthesis of 2-[4-(trimethylsilanylmethoxy)benzylidene]malonamide According to Route A

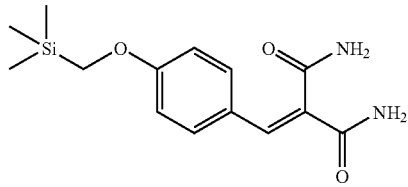

4-(Trimethylsilanylmethoxy)benzaldehyde (obtained in step 1 of Example 1) (10.4 g, 0.005 mol) and malonamide (5.5 g, 0.055 mol) in 20 ml of dry toluene in the presence of 0.5 ml of piperidine and 0.3 g of acetic acid are refluxed for 3 hours in a reactor equipped with Dean-Stark apparatus. The water formed is removed azeotropically. The mixture is cooled and the organic phase is washed twice with water. The organic phase is dried over sodium sulfate and filtered, and the solvent is evaporated off under vacuum. After recrystallization from ethanol, 7.2 g (yield: 49%) of the derivative of Example 10 are obtained in the form of an off-white powder:

| | | | |
|---|---|---|---|
| m.p. 163-164° C. | | | |
| UV (ethanol) | $\lambda_{max}$ = 310 nm, | $\epsilon_{max}$ = 20 350, | $E_{1\%}$ = 696. |

EXAMPLE 11

Synthesis of isopropyl 2-(4-trimethylsilanylmethoxy)cinnamate According to Route B

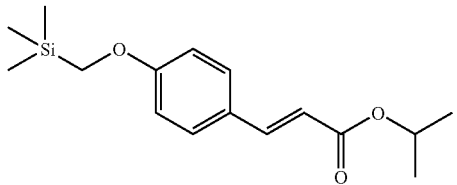

Chloromethyltrimethylsilane (0.4 ml, 2.42×10$^{-3}$ mol) is added to a mixture of isopropyl para-hydroxycinnamate (0.5 g, 2.42×10$^{-3}$ mol) and potassium carbonate (0.4 g, 2.86×10$^{-3}$ mol) in 5 ml of dry DMF maintained at 80° C., and while sparging with nitrogen. The mixture is left at 120° C. for 1 hour. The reaction mixture is cooled and poured into ice-cold water. The oily phase is extracted with dichloromethane. The organic phase is washed twice with water, dried over sodium sulfate and filtered, and the solvent is evaporated off under vacuum. The final traces of DMF are removed via a stage at 60° C. under a vacuum of 2 mmHg. The brown oil obtained is purified by chromatography on a column of silica (eluent: 95/5 heptane/EtOAc). 360 mg of clean fractions (yield: 51% of the derivative of Example 11 are recovered in the form of a pale yellow viscous oil:

| | | | |
|---|---|---|---|
| UV (ethanol) | $\lambda_{max}$ = 310 nm, | $\epsilon_{max}$ = 20 800, | $E_{1\%}$ = 711. |

EXAMPLE 12

Synthesis of di(methyltrimethylsilanyl) 2-(2-methoxybenzylidene)malonate According to Route C

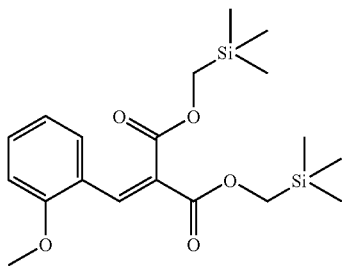

a) First Step: Preparation of di(methyltrimethylsilyl)malonate:

Malonic acid (8.3 g, 0.079 mol) and hydroxymethyltrimethylsilane (18.35 g, 0.176 mol) in 50 ml of toluene in the presence of 0.2 ml of concentrated sulfuric acid are refluxed for 3 hours in a reactor equipped with Dean-Stark apparatus. The water formed (3.1 ml) is removed azeotropically. The organic phase is washed twice with water and dried over sodium sulfate. After filtration, evaporation of the solvent under vacuum and distillation under vacuum (b.p. 73-75° C. at 0.15 mbar), 19.6 g (yield: 90%) of di(methyltrimethylsilyl) malonate are obtained in the form of a colorless oil.

b) Second Step: Synthesis of the Derivative of Example 12:

2-Methoxybenzaldehyde (0.98 g, 7.2×10$^{-3}$ mol) and di(methyltrimethylsilyl) malonate (2 g, 7.23×10$^{-3}$ mol) in 8 ml of dry toluene in the presence of 6 mg of piperidine and 5 mg of acetic acid are refluxed for 5 hours in a reactor equipped with Dean-Stark apparatus. The water formed is removed azeotropically. The mixture is cooled and the toluene is removed by distillation. The reaction mixture is taken up in diisopropyl ether. The organic phase is washed twice with water, dried over sodium sulfate and filtered, and the solvent is evaporated off under vacuum. The brown oil obtained is purified by chromatography on a column of silica (eluent: 95/5 heptane/EtOAc). 2.1 g of clean fractions (yield: 74%) of the derivative of Example 12 are recovered in the form of a colorless viscous oil:

| | | | |
|---|---|---|---|
| UV (ethanol) | $\lambda_{max}$ = 325 nm, | $\epsilon_{max}$ = 7 420, | $E_{1\%}$ = 188 |
| | $\lambda_{max}$ = 274 nm, | $\epsilon_{max}$ = 10 810, | $E_{1\%}$ = 274. |

EXAMPLE 13

Synthesis of di(methyltrimethylsilanyl) 2-(4-methoxybenzylidene)malonate According to Route C

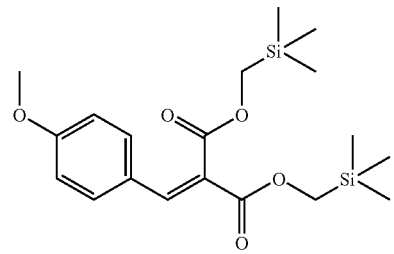

4-Methoxybenzaldehyde (12.3 g, 0.03 mol) and di(methyltrimethylsilyl) malonate (25 g, 0.09 mol) in 40 ml of dry toluene in the presence of 0.9 ml of piperidine and 0.5 ml of acetic acid are refluxed for 4 hours in a reactor equipped with Dean-Stark apparatus. The water formed is removed azeotropically. The mixture is cooled and the toluene is removed by distillation. The reaction mixture is taken up in diisopropyl ether. The organic phase is washed 3 times with water, dried over sodium sulfate and filtered, and the solvent is evaporated off under vacuum. The solid obtained is recrystallized from isopropanol to give 25.1 g (yield: 71%) of the derivative of Example 13 in the form of a white powder:

m.p.: 86° C.

UV (ethanol)  $\lambda_{max}$ = 313 nm,  $\epsilon_{max}$ = 25 770,  $E_{1\%}$ = 653.

COMPOSITION EXAMPLES

| Chemical Name | Example A W/W (%) | Example B W/W (%) |
| --- | --- | --- |
| Glyceryl monostearate/polyethylene glycol stearate mixture (100 EO) (Simulsol 165 - SEPPIC) | 1 | 1 |
| Stearic acid (Stearine TP 1200 Pastilles - Stéarinerie Dubois) | 1.5 | 1.5 |
| Polydimethylsiloxane (200 Fluid 350 CS - Dow Corning) | 0.5 | 0.5 |
| Cetyl alcohol (Lanette 16 NF - Cognis) | 0.5 | 0.5 |
| Cetearyl glucoside/cetyl stearyl alcohol mixture (Montanov 68 - SEPPIC) | 2 | 2 |
| $C_{12}$–$C_{15}$ alkyl benzoate (Finsolv TN - Witco) | 10 | 10 |
| Dimethyl 2-(4-trimethylsilanylmethoxy)-benzylidenemalonate according to Example 1 or 2 | 0.5 | 5 |
| Glycerol | 5 | 5 |
| Xanthan gum (Keltrol T - CP Kelco) | 0.2 | 0.2 |
| Crosslinked acrylic acid/$C_{10}$–$C_{30}$ alkyl acrylates copolymer (Pemulen TR1 - Noveon) | 0.2 | 0.2 |
| Isohexadecane (Isohexadecane - BP) | 1 | 1 |
| Preservative | 1 | 1 |
| Triethanolamine | 0.65 | 0.65 |
| Demineralized water | qs 100 | qs 100 |

Manufacturing Protocol:

The fatty phase is weighed out in a beaker. The aqueous phase is weighed out in the final beaker. The two phases are heated on a waterbath (80° C.). The aqueous phase is stirred and the fatty phase is poured slowly onto the aqueous phase. The mixture is emulsified with vigorous stirring (~1000 rpm). The thickener is introduced and stirring is continued for 15 to 20 minutes. At about 30° C., the formulation is neutralized and is allowed to cool to room temperature.

Measurement of the Photoprotective Efficacy (SPF):

The efficacy of these compositions is evaluated in vitro using an SPF 290 spectroradiometer sold by Optometrics and according to the Diffey-Robson method on a plate of quartz plus Transpore:

The Sun Protection Factors (SPF) obtained are:

| Compositions | SPF |
| --- | --- |
| Example A | 2.3 ± 0.2 |
| Example B | 9.7 ± 0.7 |

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological composition suited for photoprotecting keratin materials, comprising an effective UV-photoprotecting amount of at least one methyltrialkylsilane compound having the formula (I) below:

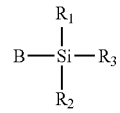

(I)

in which:

B is a chromophoric group having either of formulae (1) and (2) below:

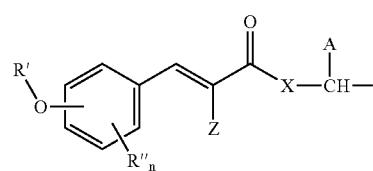

(1)

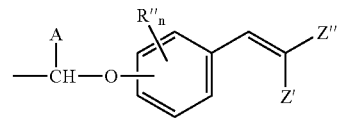

(2)

$R_1$ and $R_2$, which may be identical or different, are each a linear or branched $C_1$-$C_{12}$ alkyl radical, optionally halogenated or containing a double bond or a triple bond, or a phenyl or benzyl radical;

$R_3$ is a radical $R_1$ or $R_2$ or a group B;

n is an integer ranging from 0 to 3 inclusive;

X is —O— or —NR$_5$—;

A is a hydrogen atom, a linear or branched $C_1$-$C_4$ alkyl radical, a group $SiR_1R_2R_3$ in which $R_1$, $R_2$ and $R_3$ are as defined above, with the proviso that $R_3$ is other than B;

the radical R' is a hydrogen atom, a linear or branched $C_1$-$C_{10}$ alkyl radical, a linear or branched $C_2$-$C_8$ alkenyl radical or an $Si(CH_3)_3$ group;

the radicals R", which may be identical or different, are each a hydroxyl radical, a linear or branched $C_1$-$C_{10}$ alkyl radical, a linear or branched $C_2$-$C_8$ alkenyl radical, a linear or branched $C_1$-$C_{10}$ alkoxy radical, with the proviso that R" may together form with an adjacent R" or OR', an alkylidenedioxy group in which the alkylidene group contains one or two carbon atoms, or an —OSi(CH$_3$)$_3$ group;

Z, Z' and Z", which may be identical or different, are each a hydrogen atom, a linear or branched $C_1$-$C_4$ alkyl radical; a group —(C═O)R$_4$, —(C═O)OR$_4$, —SO$_2$R$_5$, —(C═O)NR$_6$R$_7$, —CN or —(C═O)XCHASiR$_1$R$_2$R$_3$ in which $R_1$, $R_2$ and $R_3$ are as defined above, with the proviso that $R_3$ is other than B, and with the further proviso that:

(i) at least one of the radicals Z' and Z" is other than hydrogen, and (ii) when Z' is —SO$_2$R$_5$, then Z" is other than a —CN group;

$R_4$ is a hydrogen atom or a linear or branched $C_1$-$C_{20}$ alkyl radical;

$R_5$ is a $C_1$-$C_{20}$ alkyl radical or a $C_6$-$C_{12}$ aryl radical;

R₆ and R₇, which may be identical or different, are each a hydrogen atom or a $C_1$-$C_4$ alkyl radical; with the further proviso that:

Z' and Z" may also together form a Meldrum acid of formula (3) below:

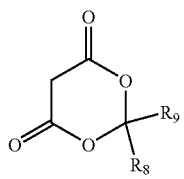

(3)

in which

R₈ and R₉, which may be identical or different, are each hydrogen or a linear or branched $C_1$-$C_{20}$ alkyl radical; and R₈ and R₉ may also together form a $C_5$-$C_{12}$ ring member, formulated into a topically applicable, cosmetically/dermatologically acceptable medium therefor.

2. The cosmetic/dermatological composition as defined by claim 1, wherein formula (I), B is a chromophoric group (1).

3. The cosmetic/dermatological composition as defined by claim 1, wherein formula (I), B is a chromophoric group (2).

4. The cosmetic/dermatological composition as defined by claim 1, wherein formula (I), R₃ is a group B.

5. The cosmetic/dermatological composition as defined by claim 2, wherein formula (I), X is —O—.

6. The cosmetic/dermatological composition as defined by claim 2, wherein formula (I), X is —NR₅.

7. The cosmetic/dermatological composition as defined by claim 2, wherein formula (I):

R₁, R₂ and R₃ are each a $C_1$-$C_4$ alkyl radical;

Z is hydrogen, COOR₄ in which R₄ is a $C_1$-$C_8$ alkyl radical, CN or —(C═O)XCHASiR₁R₂R₃;

A is a hydrogen atom;

X is O or NH;

n=0; and

R' is a $C_1$-$C_4$ alkyl radical.

8. The cosmetic/dermatological composition as defined by claim 7, wherein formula (I):

Z is COOR₄ and R₄ is methyl; and

R₁, R₂ and R₃ are each methyl.

9. The cosmetic/dermatological composition as defined by claim 1, said at least one methyltrialkylsilane compound of formula (I) being selected from the group consisting of the following compounds:

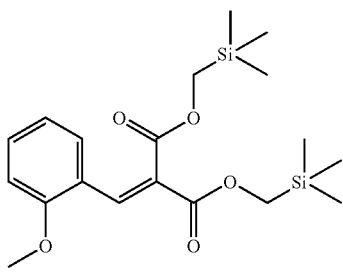

(compound a)

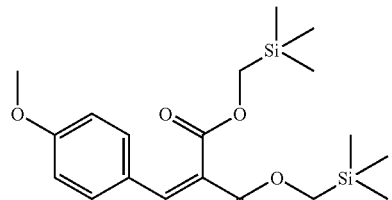

(compound b)

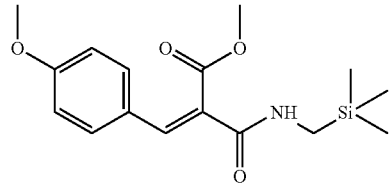

(compound c)

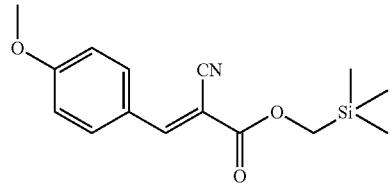

(compound d)

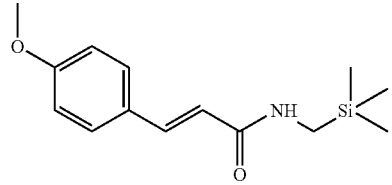

(compound e)

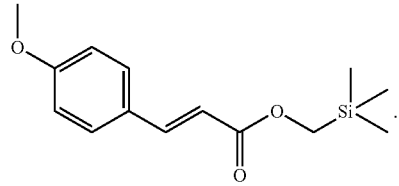

(compound f)

10. The cosmetic/dermatological composition as defined by claim 3, wherein formula (I):

A is a hydrogen atom;

R₁ and R₂ are each a $C_1$-$C_4$ alkyl radical;

n=0 or 1 and when n=1, R" is a $C_1$-$C_4$ alkoxy radical;

Z' and Z", which may be identical or different, are each a group selected from among:

1) —(C═O)OR₄ in which R₄ is a $C_1$-$C_8$ alkyl radical;

2) —(C═O)NH₂;

3) —CN;

4) or a group of formula (3) in which R₈ and R₉ are each a $C_1$-$C_4$ alkyl radical.

11. The cosmetic/dermatological composition as defined by claim 10, wherein formula (I):

R₁ and R₂ are each methyl;

Z' and Z" form a group of formula (3) and R₈ and R₉ are each methyl; and n=1 and R" is methoxy.

12. The cosmetic/dermatological composition as defined by claim 1, said at least one methyltrialkylsilane compound of formula (I) being selected from the group consisting of the following compounds:

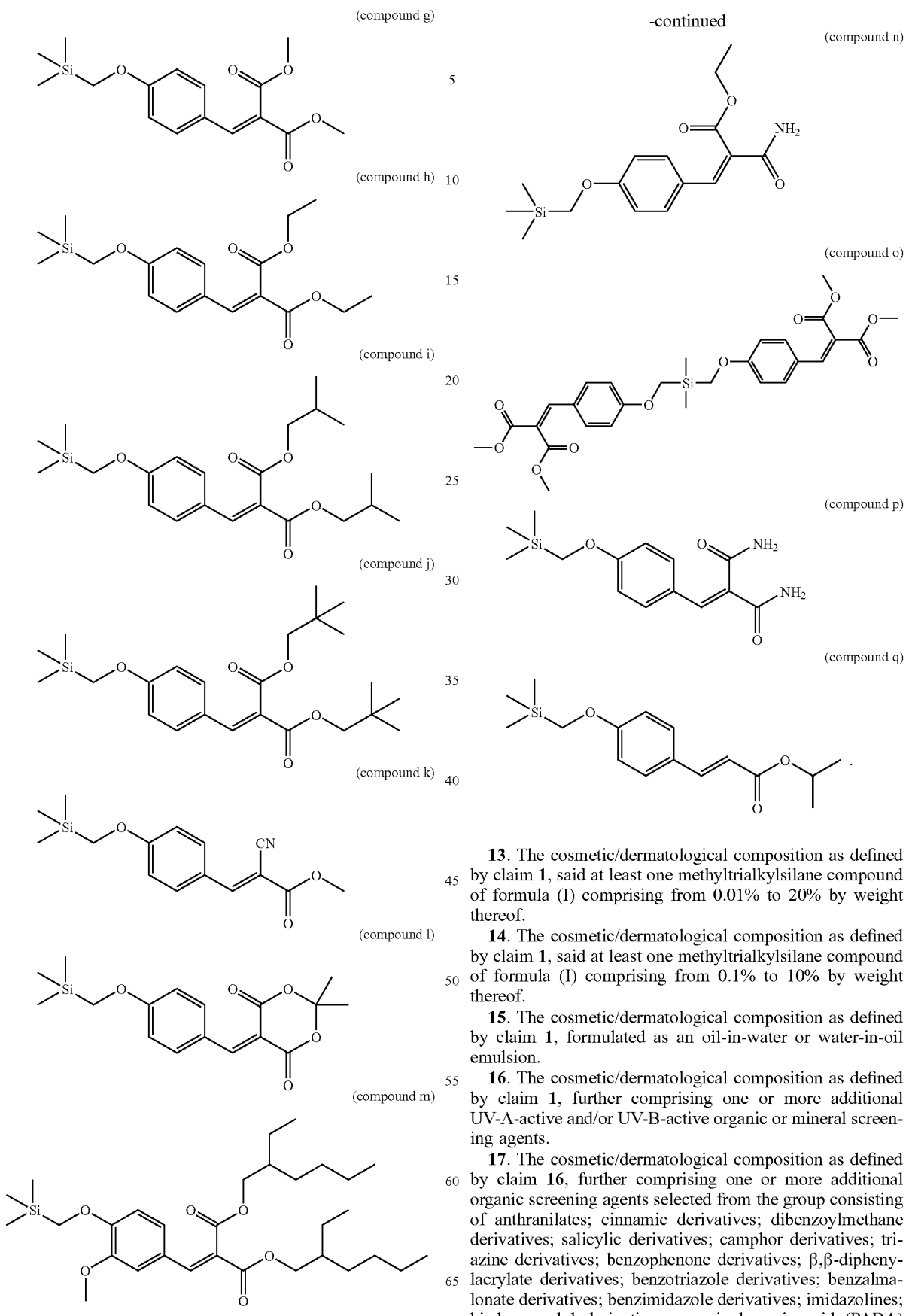

13. The cosmetic/dermatological composition as defined by claim 1, said at least one methyltrialkylsilane compound of formula (I) comprising from 0.01% to 20% by weight thereof.

14. The cosmetic/dermatological composition as defined by claim 1, said at least one methyltrialkylsilane compound of formula (I) comprising from 0.1% to 10% by weight thereof.

15. The cosmetic/dermatological composition as defined by claim 1, formulated as an oil-in-water or water-in-oil emulsion.

16. The cosmetic/dermatological composition as defined by claim 1, further comprising one or more additional UV-A-active and/or UV-B-active organic or mineral screening agents.

17. The cosmetic/dermatological composition as defined by claim 16, further comprising one or more additional organic screening agents selected from the group consisting of anthranilates; cinnamic derivatives; dibenzoylmethane derivatives; salicylic derivatives; camphor derivatives; tri- azine derivatives; benzophenone derivatives; β,β-dipheny- lacrylate derivatives; benzotriazole derivatives; benzalma- lonate derivatives; benzimidazole derivatives; imidazolines; bis-benzazolyl derivatives; p-aminobenzoic acid (PABA)

derivatives; methylenebis(hydroxyphenylbenzotriazole) derivatives; benzoxazole derivatives; screening polymers and screening silicones; dimers derived from α-alkylstyrene; 4,4-diarylbutadienes, and mixtures thereof.

18. The cosmetic/dermatological composition as defined by claim 17, further comprising one or more additional organic screening agents selected from the group consisting of:
Ethylhexyl salicylate,
Ethylhexyl methoxycinnamate,
Butyl methoxydibenzoylmethane,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
2,4,6-Tris(diisobutyl 4'-aminobenzalmalonate)-s-triazine,
Anisotriazine,
Ethylhexyltriazone,
Diethylhexylbutamidotriazone,
Methylenebis(benzotriazolyl)tetramethylbutylphenol,
Drometrizole trisiloxane,
Polysilicone-15
1,1-Dicarboxy(2,2'-dimethylpropyl)-4,4-diphenylbutadiene,
2,4-bis[5-1 (dimethylpropyl)benzoxazol-2-yl(4-phenyl)imino]-6-(2-ethylhexyl)imino-1,3,5-triazine and mixtures thereof.

19. The cosmetic/dermatological composition as defined by claim 16, further comprising one or more additional mineral screening agents which comprise coated or uncoated metal oxide pigments or nanopigments.

20. The cosmetic/dermatological composition as defined by claim 19, further comprising one or more pigments or nanopigments selected from the group consisting of titanium oxide, zinc oxide, iron oxide, zirconium oxide and cerium oxide, and mixtures thereof, whether coated or uncoated.

21. The cosmetic/dermatological composition as defined by claim 1, further comprising at least one agent for artificially tanning and/or browning the skin.

22. The cosmetic/dermatological composition as defined by claim 1, further comprising at least one adjuvant selected from the group consisting of fatty substances, organic solvents, ionic or nonionic thickeners, softeners, humectants, antioxidants, moisturizers, desquamating agents, free-radical scavengers, anti-pollution agents, anti-bacterial agents, anti-inflammatory agents, depigmenting agents, propigmenting agents, opacifiers, stabilizers, emollients, silicones, anti-foams, insect repellents, fragrances, preservatives, anionic, cationic, nonionic, zwitterionic or amphoteric surfactants, substance P antagonists, substance CGRP antagonists, fillers, pigments, polymers, propellants and acidifying or basifying agents.

23. The cosmetic/dermatological composition as defined by claim 1, formulated for photoprotecting human skin as a nonionic vesicular dispersion, a cream, a milk, a gel, a cream-gel, a suspension, a dispersion, an emulsion, an oil, a powder, a solid tube, a mousse or a spray.

24. The cosmetic/dermatological composition as defined by claim 1, formulated as a makeup for the eyelashes, the eyebrows, the nails or the skin and comprising a solid or pasty, anhydrous or aqueous form or an emulsion, a suspension or a dispersion.

25. The cosmetic/dermatological composition as defined by claim 1, formulated for protecting the hair against ultraviolet rays and comprising a shampoo, a lotion, a gel, an emulsion or a nonionic vesicular dispersion.

26. A regime or regimen for photoprotecting a keratin material against the damaging effects of UV-radiation, comprising topically applying thereon a thus effective amount of the cosmetic/dermatological composition as defined by claim 1.

27. The regime or regimen as defined by claim 26, said keratin material being human skin.

28. A regime or regimen for controlling the variation in the color of the skin caused by UV radiation, comprising topically applying thereon a thus effective amount of the cosmetic/dermatological composition as defined by claim 1.

* * * * *